United States Patent [19]
Drake et al.
[11] Patent Number: 4,678,659
[45] Date of Patent: Jul. 7, 1987

[54] THERAPEUTIC DEVICES INCORPORATING WATER SOLUBLE GLASS COMPOSITIONS

[75] Inventors: Cyril F. Drake, Harlow; John R. Brocklehurst, Bishop's Stortford, both of England

[73] Assignee: STC, plc, London, England

[21] Appl. No.: 829,067

[22] Filed: Feb. 13, 1986

Related U.S. Application Data

[63] Continuation-in-part of Ser. No. 673,273, Nov. 20, 1984, abandoned.

[30] Foreign Application Priority Data

Nov. 26, 1983 [GB] United Kingdom ................ 8331661

[51] Int. Cl.[4] ........................ A61K 9/00; A01N 11/04

[52] U.S. Cl. ...................................... 424/451; 501/11; 514/770

[58] Field of Search ....................... 424/14, 19, 23, 22; 514/770; 501/11

[56] References Cited

U.S. PATENT DOCUMENTS 4,350,675 9/1982 Drake ...................................... 424/9
4,449,981 5/1984 Drake et al. .......................... 424/19

FOREIGN PATENT DOCUMENTS 2057420 4/1981 United Kingdom .
2077585 12/1981 United Kingdom .
2077586 12/1981 United Kingdom .
2109665 6/1983 United Kingdom .
2111388 7/1983 United Kingdom .
2116424 9/1983 United Kingdom .

*Primary Examiner*—Ronald W. Griffin
*Attorney, Agent, or Firm*—Dennis P. Clarke

[57] ABSTRACT

A therapeutic material is contained in a water soluble glass having a dissolution rate that is distinctly pH sensitive, the ratio of dissolution rates between pH 2 and pH 6 being greater than 60 to 1. The glass incorporates phosphorus pentoxide as the glass former and an alkali metal oxide and one or more alkaline earth metal oxides as glass modifiers.

7 Claims, No Drawings

THERAPEUTIC DEVICES INCORPORATING WATER SOLUBLE GLASS COMPOSITIONS

RELATED APPLICATIONS

This application is a continuation-in-part of application Ser. No. 673,273, filed Nov. 20, 1984, now abandoned.

BACKGROUND OF THE INVENTION

This invention relates to therapeutic devices incorporating water soluble glass compositions whose dissolution rate is strongly dependent on the pH of a surrounding aqueous medium.

Water-soluble glass compositions are finding a variety of uses in medical and veterinary applications for the controlled release of one or more active materials. There are special circumstances and particular types of product where it is desirable that the rate of solution of a glass should change rapidly when the pH of the aqueous medium is changed. For example, in some cases where a pharmaceutical product is to be delivered orally, e.g., as a tablet or bolus or as a granular material, it may be desirable that none should be delivered during the transport of the material from mouth to stomach but that the product should be delivered rapidly as soon as the product reaches the stomach.

A similar product arises when administering therapeutic materials, e.g., methionine, to ruminant animals. Many of these materials degrade under the alkaline conditions pertaining in the rumen and thus, with conventional delivery devices, very little material is delivered to the animal. This problem is further aggravated by the digestive process of a ruminant animal. Food is retained in the rumen for several hours, but the contents of the rumen are passed through the remainder of the digestive tract in a relatively short time.

An object of the present invention is to provide a delivery system that is inert under high pH conditions but becomes active under low pH conditions.

SUMMARY OF THE INVENTION

The present invention provides a therapeutic device for oral administration to the alimentary tract, the device being readily soluble in that part of the alimentary tract where low pH conditions pertain but which is of low solubility under high pH conditions, the device comprising a sealed capsule of a water soluble glass containing a therapeutic material, wherein said glass comprises phosphorus pentoxide as the glass forming oxide, a first glass modifying oxide ($M_2O$) selected from the group coprising alkali metal oxides and mixtures thereof, and a second glass modifying oxide (M'O) selected from the group comprising alkaline earth metal oxides, zinc oxide, cupric oxide and mixtures thereof, and wherein the glass has a composition selected from the range 25.0 to 40.3 mole % $M_2O$, 25.0 to 35.0 mole % M'O and 33.6 to 45 mole % $P_2O_5$, the composition being such that the ratio of the dissolution rates of the glass at pH 2 and at pH 6, respectively, is at least 60 to 1.

DETAILED DESCRIPTION OF THE INVENTION

If the therapeutic material is enclosed in a capsule comprising a glass the rate of solution of which is two orders of magnitude greater at pH 1–2 than at pH 6–8 then, if the composition of the glass is selected so that it will dissolve completely in one hour at pH 6, it will dissolve completely in less than one minute at pH 1–2, e.g., the pH conditions pertaining in the human stomach, thereby releasing the contained therapeutic material.

It has been found that it is possible to select composition ranges of water-soluble phosphate glass whose dissolution rates show a strong dependence on the pH conditions.

The composition of the glasses is herein described in terms of the mole percent of the normal oxides of the elements which they contain. This conventional method of describing the composition does not imply that these oxides are used to prepare the glass batch, as other compounds of the elements such as carbonates, sulfates, hydroxides, etc., which decompose to the oxide at the temperature of the glass melt may optionally be used in the batch. Nor does the method of describing the composition necessarily imply that such oxides are present as discrete molecules of the oxides in the glass.

The constituent oxides in the glass will be classified, conventionally, as glass-forming oxides and glass-modifying oxides. In the case of the glasses disclosed herein, the glass-forming oxide is $P_2O_5$ and the glass-modifying oxides are alkali-metal oxides ($M_2O$), alkaline earth metal oxides and optionally other divalent metal oxides (M'O) and optionally metal sesquioxides ($M_2''O_3$), such as $Al_2O_3$ or $Fe_2O_3$. A small proportion of $P_2O_5$ may be replaced by another glass-forming oxide such as $SiO_2$, $B_2O_3$, or $SeO_2$ without substantially changing the behavior of the glass. A small proportion of the glass-modifying oxide may be a metal oxide not included by the above definitions, e.g., to provide trace elements. A trace proportion of fluoride, chloride, bromide or iodide ions and/or a trace of a precious metal such as Au or Pt, which is preferably present as colloidal or atomic zero-valent particles, may be included in specialized applications.

The therapeutic material may comprise inter alia an antibiotic, a growth promoter such as methionine, or an anthelmintic. In some applications the glass may contain a metal that has a synergistic effect with the therapeutic material. For example, a copper-containing glass can be used with an anthelmintic to improve its efficiency.

To ensure that substantially no dissolution takes place at pH 6 whereas rapid dissolution takes place at pH 2 we employ a dissolution rate ratio at pH 2/pH 6 greater than or equal to 60 to 1. This ensures, for example, that when the device is applied to a ruminant animal there is little dissolution during the extended period in the rumen but there is complete dissolution during the rapid passage through the post rumen to release the device contents.

The glasses are formed by melting their constituent materials in oxide form or in the form of compounds which decompose on heating to form oxides, to obtain an homogeneous melt. This melt is then cast or drawn into tubular form. As some phosphorus pentoxide is lost during melting, it is preferred to determine the glass composition by chemical analysis of the finished material. Tubular sections of the glass are filled or partly filled with the therapeutic material and flame sealed at both ends to provide a capsule.

The pH-dependence of the solution rate of the glasses has been measured by placing small specimens of the glass in an open gauge basket in flowing solutions of various pH values and determining the weight loss with time. Typical results are shown in Table I below. The compositions are expressed in mole percentage of oxides.

TABLE I

| Glass No. | $Na_2O$ | $P_2O_5$ | CaO | MgO | ZnO | CuO | Solubility Ratio pH2/pH6 |
|---|---|---|---|---|---|---|---|
| 1 | 25.0 | 40.0 | 35.0 | — | — | — | 200 |
| 2 | 40.3 | 43.0 | 7.8 | 8.8 | — | — | 79 |
| 3 | 25.0 | 44.6 | 30.2 | — | — | — | 68 |
| 4 | 36.4 | 33.6 | — | — | 10 | 20 | 1200 |
| 5 | 30.0 | 45.0 | 25.0 | — | — | — | 800 |
| 6 | 33.0 | 41.2 | — | 25.8 | — | — | 100 |

It has been found that generally in glasses of the formula, $xM_2O.y M'O. (100-x-y)P_2O_5$, where x and y are the molar percentages of $M_2O$ and M'O respectively, a decrease in the mole percentage of $P_2O_5$ and a decrease in the mole percentage of $M_2O$ in the glass increases the pH-dependence of the solution rate.

Moreover, in glasses with a given value of x and y, addition of small amounts of a metal sesquioxide, e.g., aluminium, to the base glass increases substantially the pH-dependence of the solution rate.

It will be clear that by selection of the composition in terms of the three variables, (mole %) $P_2O_5$, $M_2O$ and M'O, it is possible to find a composition which combines a chosen absolute level of solution rate with a high pH dependence of solution rate. In particular it has been have found that glass compositions in the range 36 to 36.5 $M_2O$, 33.5 to 34 $P_2O_5$, 29.5 to 30.5 M'O have dissolution rate ratios at pH 2 and pH 6 greater than or equal to 1,000 to 1.

The limits of the composition ranges which can be used are, of course, ultimately set by the limits of composition which will form glasses on cooling from the melt. It is well known to those skilled in the art that the glass-forming region is usually extended by the addition of more constituents to a given system. If additional constituents are added, some adjustments, which can be determined experimentally, will have to be made to the glass-forming limits of these figures but it has been found that the limits of the composition ranges, which have a large change of solution rate with pH, are not sensibly altered.

It has been found that the glass compositions with the highest pH dependence of solution rates are found in the region with a mole ratio $Na_2O/P_2O_5$21 1 and with $P_2O_5 < 45$ mole %. Preferably the glass has a dissolution rate at pH 2 greater than 25 mg/cm$^2$/day.

The following example illustrates the invention.

EXAMPLE 1

A glass was prepared by melting a mix containing 1920 g $NaH_2PO_4$; 216 g $CaHPO_4$; 164 g 3 Mg $CO_3$.Mg$(OH)_2$.3$H_2O$; and 20 g $Na_2CO_3$ in a platinum crucible for 1 hr in air at 1150° C. The weight loss during fusion was 415 g. The glass composition was that of glass No. 2 of Table 1.

The molten glass was then cast to form stock tube 40 mm in diameter. Samples of this stock tube were drawn down to a diameter of 2.02 mm and a wall thickness of 0.20 mm. The drawn tube was cut into lengths of 12 mm and each length was partly filled with methionine together with a methylene blue dye tracer. The tubes were then flame sealed at both ends.

The sealed tubes were immersed in water samples at a temperature of 38° C. and of pH 2.0; 3.0; 4,0; and 6.0. In each case the delay time before release of the dye indicating dissolution of the glass was measured, the results being summarized in Table II below.

TABLE II

| Solution pH | 2.0 | 3.0 | 4.0 | 6.0 |
|---|---|---|---|---|
| Delay time Hr | 1.0 | 19 | 40 | 70 |

This example illustrates the feasibility of preparing therapeutic devices using the technique described herein.

EXAMPLE 2

To illustrate the invention a glass (Composition 2 in Table 1) was prepared by forming a mixture of $NaH_2PO_4$, $CaHPO_4$, $MgCO_3$, $Mg(OH_2).3H_2O$ and $Na_2CO_3$ in a platinum crucible in air at 1150° C. The melt was then drawn into stock tube 40 mm in diameter. Samples of this stock was drawn down to a diameter of 2.02 mm and a wall thickness of 0.20 mm. The drawn tube was cut into lengths of 12 mm and each length was partly filled with methionine together with a methylene blue dye tracer. The tubes were then flame sealed at both ends.

The sealed tubes were immersed in water samples at a temperature of 38° C. and of pH2; 3; 4 and 6. In each case the delay time before release of the dye tracer indicating dissolution of the glass was measured, the results being summarized below.

TABLE III

| Solution pH | 2.0 | 3.0 | 4.0 | 6.0 |
|---|---|---|---|---|
| Delay Time Hr | 1.0 | 19 | 40 | 70 |

It will be appreciated that the temperature of 38° C. and the aqueous environments of pH 2 and pH 6 correspond to the conditions pertaining in the digestive system of a ruminant animal.

We claim:

1. A therapeutic device for oral administration to the alimentary tract, the device being readily soluble in that part of the alimentary tract where low pH conditions pertain but which is of low solubility under high pH conditions, the device comprising a sealed capsule of a water soluble glass containing a therapeutic material, wherein said glass comprises phosphorus pentoxide as the glass forming oxide, a first glass modifying oxide ($M_2O$) selected from the group consisting of alkali metal oxides and mixtures thereof, and a second glass modifying oxide (M'O) selected from the group consisting of alkaline earth metal oxides, zinc oxide, cupric oxide and mixtures thereof, and wherein the glass has a composition selected from the range 25.0 to 40.3 mole % $M_2O$, 25.0 to 35.0 mole % M'O and 33.5 to 45 mole % $P_2O_5$, the composition being such that the ratio of the dissolution rates of the glass at pH 2 and at pH 6 is at least 60 to 1, whereby in use, when in contact with a part of the alimentary tract where low pH conditions pertain, rapid dissolution of the capsule is effected to provide release of the therapeutic material as a single dose.

2. A device as claimed in claim 1 and incorporating an animal feed additive.

3. A device as claimed in claim 2, wherein the feed additive is methionine.

4. A device as claimed in claim 1, wherein the therapeutic material is an anthelmintic.

5. A device as claimed in claim 4, wherein the glass contains copper.

6. A device as claimed in claim 1, wherein the glass comprises 36 to 36.5 mole % $M_2O$; 33.5 to 34 mole % $P_2O_5$ and 29.5 to 30.5 mole % M'O, the coposition being such that the dissolution rate ratio pH2/pH6 is greater than or equal to 1,000 to 1.

7. A device as claimed in claim 1, wherein the glass dissolution rate in water at 38° C. and at pH 2 is greater than 25 $mg/cm^2/day$.

* * * * *